United States Patent [19]

Wilson, II

[11] Patent Number: 4,457,922

[45] Date of Patent: Jul. 3, 1984

[54] PESTICIDAL BISPHENOL PHOSPHATES

[75] Inventor: Charles A. Wilson, II, Raleigh, N.C.

[73] Assignee: Union Carbide Corporation, Danbury, Conn.

[21] Appl. No.: 363,832

[22] Filed: Mar. 31, 1982

[51] Int. Cl.$^3$ .................. A01N 57/14; C07F 9/165
[52] U.S. Cl. ............................. 424/206; 260/929; 260/930
[58] Field of Search ............... 260/929, 930; 424/206

[56] References Cited

U.S. PATENT DOCUMENTS

| 3,153,663 | 10/1964 | Sirrenberg et al. | 260/929 |
| 3,159,533 | 12/1964 | Nelson | 260/930 |
| 3,317,636 | 5/1967 | Lovell et al. | 260/929 |
| 3,725,514 | 4/1973 | Tsuchiya et al. | 260/964 |
| 3,876,666 | 4/1975 | Oswald et al. | 260/930 |

Primary Examiner—Anton H. Sutto
Attorney, Agent, or Firm—J. A. Shedden; J. D. Wood

[57] ABSTRACT

This invention relates to compositions and the synthesis thereof of novel phosphorous esters of bisphenols which are effective broad spectrum acaricides and insecticides.

15 Claims, No Drawings

PESTICIDAL BISPHENOL PHOSPHATES

This invention relates to novel insecticidal and miticidal phosphorous esters of bisphenols. This invention also relates to pesticidal compositions for controlling insects and mites, as well as to methods of controlling insects and mites by subjecting them to an insecticidally or miticidally effective amount of a compound of this invention.

The novel compounds of this invention are compounds of the formula:

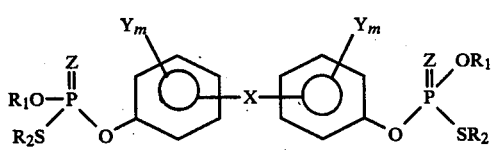

wherein:
$R_1$ and $R_2$ are individually $C_1$ to $C_6$ alkyl;
X is $C_2$ to $C_8$ alkylene, $S(O)_n$, O, $CR_3R_4$, or CQ;
n is 0, 1 or 2;
$R_3$ and $R_4$ are individually hydrogen, $C_1$ to $C_6$ alkyl, $C_1$ to $C_6$ alkoxy or together form a divalent ring of 3 to 7 carbon or carbon and oxygen atoms wherein any two adjacent carbon atoms can also be part of a fused aromatic ring system;
Q is O, $NOR_5$ or $CY_2$;
$R_5$ is $C_1$ to $C_6$ alkyl, arylalkyl or substituted arylalkyl;
Y is hydrogen, halogen or $C_1$ to $C_6$ alkyl;
Z is oxygen or sulfur; and
m is 1 or 2.

Generally, the preferred compounds of this invention are those wherein:
$R_1$ and $R_2$ are individually $C_2$ to $C_4$ alkyl;
X is $S(O)_n$, O, $CR_3R_4$ or CQ;
n is 0, 1 or 2;
$R_3$ and $R_4$ are individually hydrogen, $C_1$ to $C_6$ alkyl, $C_1$ to $C_6$ alkoxy, or together form a divalent ring of 5 to 7 carbon atoms;
Q is O, $NOR_5$ or $CY_2$;
$R_5$ is $C_1$ to $C_6$ alkyl;
Y is hydrogen, halogen or $C_1$ to $C_6$ alkyl;
Z is oxygen or sulfur; and
m is 1 or 2.

Generally, the more preferred compounds of this invention are those wherein:
$R_1$ and $R_2$ are individually $C_2$ to $C_4$ alkyl;
X is $S(O)_n$, O, $CR_3R_4$ or CQ;
n is 0, 1 or 2;
$R_3$ and $R_4$ are individually hydrogen or $C_1$ to $C_6$ alkyl;
Q is O, $NOR_5$ or $CCl_2$;
$R_5$ is $C_2$ to $C_6$ alkyl;
Y is hydrogen, halogen or $C_1$ to $C_6$ alkyl;
Z is oxygen; and
m is 1 or 2.

The novel phosphorous esters of the substituted bisphenols of this invention can be conveniently prepared by the general reaction method or a modification thereof set forth below.

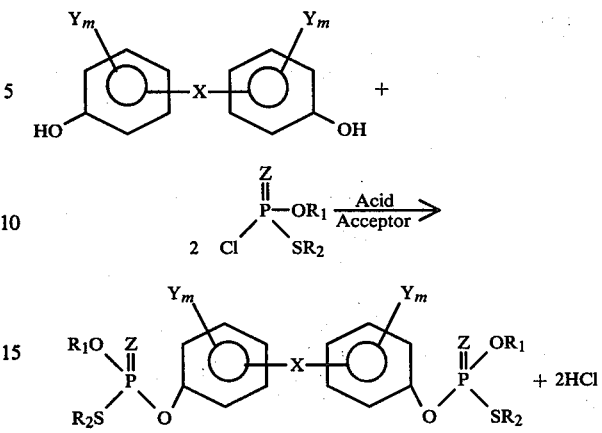

In the above reaction scheme, $R_1$, $R_2$, X, Y, Z, and m have the meanings given in the generic formula (vide supra).

In this reaction, one equivalent of the precursor bisphenol reacts with two equivalents of the appropriate cholorophosphorous compound in the presence of at least two equivalents of an acid acceptor (base), preferably in an inert solvent.

In general, any organic solvent that is inert to the reactants or reaction conditions may be employed in the reaction schemes shown above. Illustrative solvents which are suitable in the phosphorylation reaction are saturated, unsaturated, and aromatic hydrocarbons, e.g., hexane, cyclohexane, octane, cyclohexene, dodecane, naphtha, decalin, kerosene, cycloheptane, benzene, toluene, xylene, naphthalene, or the like; ethers such as dioxane, tetrahydrofuran, diethyl ether, tetrahydropyran, 1,2-dimethoxybenzene, the dialkyl ethers of ethylene glycol, of propylene glycol, or chlorinated aliphatic hydrocarbons such as chloroform, dichloromethane, 1,1-dichloroethane, carbon tetrachloride, and the like.

The phosphorylation reaction illustrated above may also be conducted in a solvent which functions as an acid acceptor. Illustrative of such solvents are N,N-dimethylaniline, pyridine, alpha-picoline, any lutidine, collidine or similar aromatic or heterocyclic tertiary amine compound.

The acid acceptor utilized in these reactions can be either organic or inorganic bases. Illustrative of organic bases that are useful acid acceptors are tertiary amines such as triethylamine, pyridine, trimethylamine, 4-dimethylaminopyridine, or 1,4-diazabicyclo[2.2.2]octane. Bases such as sodium carbonate, potassium carbonate, sodium acetate, and sodium hydroxide are illustrative of useful inorganic bases.

The reaction set forth above is neither temperature nor pressure sensitive and can be conducted over a broad range of temperatures and pressures to yield the desired product. Preferably these reactions are conducted at a temperature of from about $-40°$ C. to about $140°$ C. and at atmospheric or autogeneous pressure.

The phosphorous halides utilized as reactants in the above scheme generally are known compounds in the art and can be obtained from commercial sources or prepared in accordance with conventional methods known to those skilled in the art.

The bisphenols utilized as starting materials in the above scheme are known compounds or can be prepared in accordance with conventional methods known to those skilled in the art.

The following examples are illustrative of methods utilized in the preparation of the novel compounds of the invention:

EXAMPLE 1

Preparation of 2,2-bis[4-[(ethoxy)(propylthio)phosphoryloxy]phenyl]propane

To a 250 ml round bottom flask equipped with a water condenser, drying tube, magnetic stirrer, and addition funnel was added 4,4'-isopropylidenediphenol (4.57 g, 20 mmol), triethylamine (4.24 g, 42 mmol), and acetonitrile (75 ml). The solution was cooled to 10° C. and O-ethyl S-n-propyl phosphorochloridothioate (8.30 g, 41 mmol) in acetonitrile (25 ml) was added dropwise over 15 minutes. The cooling bath was removed and the reaction warmed to 35° C. for 4 hours. The reaction was diluted with ether (500 ml) and washed successively with water (2×50 ml), 1M NaOH (2×50 ml), 1% HCl (2×50 ml), and brine (2×50 ml). The organic solution was dried (MgSO$_4$) and concentrated under reduced pressure to give the desired product as a colorless oil (6.50 g, 10.8 mmol).

Calcd. for $C_{25}H_{38}O_6P_2S_2$:C,53.56;H,6.84; Found: C,53.97;H,7.05.

EXAMPLE 2

Preparation of bis [4-[(ethoxy)(propylthio)phosphoryloxy]phenyl]sulfide

To a 250 ml round bottom flask was added 4,4'-thiodiphenol (4.36 g, 20 mmol), O-ethyl S-n-propyl phosphorochloridothioate (9.12 g, 45 mmol), powdered potassium hydroxide (3.37 g, 60 mmol), dicyclohexano-18-crown-6 (catalytic quantity), and acetonitrile. This mixture was refluxed 14 hours, cooled to room temperature, and the organic soluble fraction decanted from the solids. The organic solution was diluted with ether and successively washed with 4M NaOH (3×100 ml), water (2×50 ml), 5% HCl (1×50 ml), water (2×50 ml), and brine (2×50 ml). After drying (MgSO$_4$) the solution was concentrated under reduced pressure to give a colorless oil (4.8 g, 7.6 mmol).

Calcd. for $C_{22}H_{32}O_6P_2O_3$:C, 47.99; H, 5.86; Found: C, 47.63; H, 6.34.

The following compounds are illustrative of this invention all of which can be conveniently prepared by the processes of this invention simply by selecting appropriate starting materials.

2,2-bis[4-[(ethoxy)(propylthio)phosphoryloxy]phenyl]propane
2,2-bis[2,6-dichloro-4-[(ethoxy)(propylthio)phosphoryloxy]phenyl]propane
2,2-bis[4-[(ethoxy)(propylthio)phosphoryloxy]phenyl]butane
bis[4-[(ethoxy)(propylthio)phosphoryloxy]phenyl]sulfone
bis[4-[(ethoxy)(propylthio)phosphoryloxy]phenyl]sulfide
bis[4-[(ethoxy)(propylthio)phosphoryloxy]]phenyl]sulfoxide
bis[4-[(ethoxy)(propylthio)phosphoryloxy]phenyl]methane
1,2-bis[4-[(ethoxy)(propylthio)phosphoryloxy]phenyl]ethane
1,4-bis[4-[(ethoxy)(propylthio)phosphoryloxy]phenyl]butane
3,3-bis[4-[(ethoxy)(propylthio)phosphoryloxy]phenyl]phthalide
1,1-bis[4-[(ethoxy)(propylthio)phosphoryloxy]phenyl]cyclohexane
1,1-bis[4-[(ethoxy)(propylthio)phosphoryloxy]phenyl]cyclopentane
bis[4-[(ethoxy)(propylthio)phosphoryloxy]-phenyl]ether-2,2-bis[4-[(ethoxy)(propylthio)thiophosphoryloxy]phenyl]propane
4,4'-bis[(ethoxy)(propylthio)phosphoryloxy]benzophenone
1,1-dichloro-2,2-bis[4-[(ethoxy)(propylthio)phosphoryloxy]phenyl]ethylene
2,2-bis[3-bromo-4-[(ethoxy)(propylthio)phosphoryloxy]phenyl]propane
2,2-bis[4-[(ethoxy)(propylthio)thiophosphoryloxy]-3-methylphenyl]propane
bis[3-chloro-4-[(ethoxy)(propylthio)phosphoryloxy]phenyl]sulfide
bis[4-[(ethoxy)(propylthio)phosphoryloxy]-3-methylphenyl]ether
4,4'-bis[(ethoxy)(propylthio)phosphoryloxy]benzophenone diethyl ketal
4,4'-bis[(ethoxy)(propylthio)phosphoryloxy]benzophenone oxime methyl ether
2,2'-bis[2-[(ethoxy)(propylthio)phosphoryloxy]phenyl]propane
2,2'-bis[2,4'-bis[(ethoxy)(propylthio)phosphoryloxy]phenyl]propane Selected species of the new compounds were evaluated to determine their pesticidal activity against mites, mite eggs, an aphid, a caterpillar, a beetle, and a fly.

Suspensions of the test compounds were prepared by dissolving one gram of compound in 50 ml of acetone in which had been dissolved 0.1 g (10 percent of the weight of the compound) of an alkylphenoxy polyethoxyethanol surfactant, as an emulsifying or dispersing agent. The resulting solution was mixed into 150 ml of water to give roughly 200 ml of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

BEAN APHID FOLIAGE SPRAY TEST

Adults and nymphal stages of the bean aphid (*Aphis fabae* Scop.) reared on potted dwarf nasturtium plants at 68°-70° F. and 50±5 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids were placed on a revolving turntable and sprayed with 100-110 milliliters of test compound formulation by use of a DeVilbiss spray gun set at 40 psig air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°–70° F. and 50±5 percent, respectively. Aphids which fell onto the paper and were unable to remain standing after being uprighted were considered dead. Aphids remaining on the plant were observed closely for movement and those which were unable to move the length of the body upon stimulation by prodding were considered dead. Percent morality was recorded for various concentration levels.

SOUTHERN ARMYWORM LEAF SPRAY BAIT TEST

Larvae of the southern armyworm (*Spodoptera eridania*, (Cram.)), reared on Tendergreen bean plants at a temperature of 80+5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulations by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

MEXICAN BEAN BEETLE LEAF SPRAY TEST

Fourth instar larvae of the Mexican bean beetle (*Epilachna varivestis*, Muls.), reared on Tendergreen bean plants at a temperature of 80±5 F. and 50±5 percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5 F., for three days. Although the larvae could easily consume the leaf within 24 to 48 hours, no more food was added. Larvae which were unable to move the length of the body even upon stimulation, were considered dead.

SOUTHERN ARMYWORM OVICIDE TEST

The test organism was the egg of the Southern armyworm (*Spodoptera eridania* (Cram.)) as obtained from adults reared on Tendergreen bean plants at a temperature of 80°± F. and a relative humidity of 50±5 percent. The eggs were laid on freezer paper (Marlon 717, Copco paper). The paper was then cut into small sections containing one or two egg masses.

The test compounds were formulated by diluting the stock suspension with water to give a suspension containing 500 parts of test compound per million parts of final formulation. The egg masses were dipped until they were thoroughly wet (5–10 seconds). They were then placed on a paper towel face up and were allowed to dry for 15–30 minutes. The dry eggs were placed in a 15×60 mm petri dish containing a cotton dental wick saturated with a 5 percent sodium chloride solution to maintain a high level of humidity. The closed dishes were labeled and held at a temperature of 80°±5° F. for four days. Larvae that emerged from the eggs, even if dead at the time of observation, were recorded as hatched.

MITE FOLIAGE SPRAY TEST

Adults and nymphal stage of the two-spotted mite (*Tetranychus urticae*, Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 mites, a sufficient number for testing, were transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which last 25 seconds, was sufficient to wet the plants to run-off. As a control, 100–110 milliliters of a water solution containing acetone and emulsifier in the same concentrations as the test compound formulations, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

FLY BAIT TEST

Four to six day old adult house flies (*Musca domestica*, L.), reared according to the specifications of the Chemical Specialties Manufactureing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty-five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty-four hours, at a temperature of 80°±20° F. and a relative humidity of 50±5 percent. Flies which showed no sign of movement on prodding were considered dead.

The results of these tests together with physical properties of the tested compounds are set forth in Table I below. In these tests the pesticidal activity of the compounds at the indicated dosage rate against aphid, mite, Southern Armyworm, Bean Beetle, and housefly was rated as follows:

A=excellent control (complete kill) at 500 ppm
B=partial control (moderate kill) at 500 ppm
C=no control (little or no kill) at 500 ppm The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder, dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein control the population of insects, mites and of ova mites and insects upon plants or other material to which the pesticides are applied. Generally, when used in sufficient amount to kill or repel the insects, they do not burn or injure the plant. The toxicants are compatible with substantially any other constituents of the spray schedule, and they may be used in the soil, upon the seeds, or the roots of plant without injuring either the seeds or roots of plants. They may also be use in combination with other pesticidally active compounds.

TABLE 1

BIOLOGICAL AND ANALYTICAL PROPERTIES OF THE COMPOUNDS OF THIS INVENTION

| EXAMPLE | COMPOUND | ANALYTICAL | BEAN APHID | MITE ADULT | SOUTHERN ARMY WORM | MEXICAN BEAN BEATLE | HOUSE FLY |
|---|---|---|---|---|---|---|---|
| 1 | 2,2-bis [4-[(ethoxy) (propylthio)-phosphoryloxy]phenyl]propane | $C_{25}H_{38}O_6P_2S_2$ CALC: C, 53.56; H, 6.84 FOUND: C, 53.97; H, 7.05 | B | A | A | A | A |
| 2 | 2,2-bis [2,6-dichloro-4-[(ethoxy)-(propylthio)phosphoryloxy]phenyl]propane | $C_{25}H_{34}Cl_4O_6P_2S_2$ CALC: C, 42.99; H, 4.92 FOUND: C, 43.50; H, 5.13 | B | A | A | A | A |
| 3 | 2,2-bis[4-[(ethoxy) (propylthio)-phosphoryloxy]phenyl]butane | $C_{26}H_{40}O_6P_2S_2$ CALC: C, 54.34; H, 7.03 FOUND: C, 54.04; H, 7.37 | A | A | A | A | A |
| 4 | bis[4-[(ethoxy) (propylthio)-phosphoryloxy]phenyl]sulfone | $C_{22}H_{32}O_8P_2S_3$ CALC: C, 45.35; H, 5.54 FOUND: C, 45.05; H, 601 | C | A | A | A | A |
| 5 | bis[4-[(ethoxy) (propylthio)-phosphoryloxy]phenyl]sulfide | $C_{22}H_{32}O_6P_2O_3$ CALC: C, 47.99; H, 5.86 FOUND: C, 47.63; H, 6.34 | A | A | A | A | A |
| 6 | bis[4-[(ethoxy) (propylthio)-phosphoryloxy]phenyl]methane | $C_{23}H_{34}O_6P_2S_2$ CALC: C, 51.87; H 6.45 FOUND: C, 52.46; H, 6.55 | A | A | A | A | A |
| 7 | 3,3-bis[4-[(ethoxy) (propylthio)-phosphoryloxy]phenyl]phthalide | $C_{30}H_{36}O_8P_2S_2$ CALC: C, 55.37; H, 5,58 FOUND: C, 54.54; H, 5.55 | C | B | A | A | A |
| 8 | 1,1-bis[4-[(ethoxy) (propylthio)-phosphoryloxy]phenyl]cyclohexane | $C_{28}H_{42}O_6P_2S_2$ CALC: C, 55.98; H, 7.06 FOUND: C, 55.83; H, 7.39 | C | A | A | A | A |
| 9 | bis[4-[(ethoxy) (propylthio)- | $C_{22}H_{32}O_7P_2S_2$ | A | A | A | A | A |

TABLE 1-continued
BIOLOGICAL AND ANALYTICAL PROPERTIES OF THE COMPOUNDS OF THIS INVENTION

| EXAMPLE | COMPOUND | ANALYTICAL | BIOLOGICAL ACTIVITY | | | | |
|---|---|---|---|---|---|---|---|
| | | | BEAN APHID | MITE ADULT | SOUTHERN ARMY WORM | MEXICAN BEAN BEATLE | HOUSE FLY |
| | phosphoryloxy]phenyl]ether | CALC: C, 49.43; H, 6.05 FOUND: C, 50.08; H, 6.10 | | | | | |
| 10 | 2,2-bis[4-[(ethoxy) (propylthio)-thiophosphoryloxy]phenyl]propane | $C_{25}H_{38}O_4P_2S_4$ CALC: C, 50.65; H, 6.47 FOUND: C, 49.05; H, 6.50 | C | C | A | A | C |
| 11 | 4,4'-bis[(ethoxy) (propylthio)-phosphoryloxy]benzophenone | $C_{23}H_{32}O_7P_2S_2$ CALC: C, 50.54; H, 5.91 FOUND: C, 49.88; H, 5.82 | A | A | A | A | A |
| 12 | 1,1-dichloro-2,2-bis[4-[(ethoxy)-(propylthio)phosphoryloxy]phenyl]-ethylene | $C_{24}H_{32}Cl_2O_6P_2S_2$ CALC: C, 46.98; H, 5.26 FOUND: C, 46.06; H, 5.57 | C | A | A | A | A |

I claim:

1. A method of controlling insects and mites which comprises subjecting them to an insecticidally or miticidally effective amount of a compound of the formula:

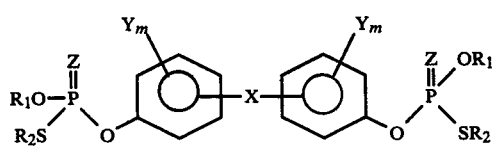

wherein:
$R_1$ and $R_2$ are individually $C_1$ to $C_6$ alkyl;
X is $C_2$ to $C_8$ alkylene, $S(O)_n$, O, $CR_3R_4$ or CQ;
n is 0, 1 or 2;
$R_3$ and $R_4$ are individually hydrogen, $C_1$ to $C_6$ alkyl, $C_1$ to $C_6$ alkoxy or together form a divalent ring of 2 to 6 carbon or carbon and oxygen atoms wherein any two adjacent carbon atoms can also be part of a fused aromatic ring system;
Q is O, $NOR_5$ or $CY_2$;
$R_5$ is $C_1$ to $C_6$ alkyl, arylalkyl or substituted arylalkyl;
Y is hydrogen, halogen or $C_1$ to $C_6$ alkyl;
Z is oxygen or sulfur; and
m is 1 or 2.

2. A method in accordance with claim 1 wherein:
$R_1$ and $R_2$ are individually $C_2$ to $C_4$ alkyl;
X is $S(O)_n$, O, $CR_3R_4$ or CQ;
$R_3$ and $R_4$ are individually hydrogen, $C_1$ to $C_6$ alkyl, $C_1$ to $C_6$ alkoxy, or together form a divalent ring of 5 to 7 carbon atoms; and
$R_5$ is $C_1$ to $C_6$ alkyl.

3. A method in accordance with claim 2 wherein:
$R_3$ and $R_4$ are individually hydrogen or $C_1$ to $C_6$ alkyl;
Q is O, $NOR_5$ or $CCl_2$; and
Z is oxygen.

4. A method in accordance with claim 1 wherein the compound is 2,2-bis[4-[(ethoxy)(propylthio)phosphoryloxy]phenyl]propane.

5. A method in accordance with claim 1 wherein the compound is bis[4-[(ethoxy)(propylthio)phosphoxyloxy]phenyl]sulfide.

6. Compounds of the formula:

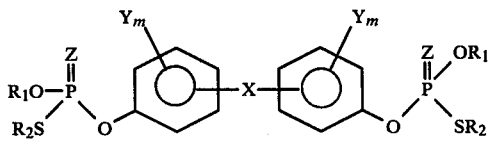

wherein:
$R_1$ and $R_2$ are individually $C_1$ to $C_6$ alkyl;
X is $C_2$ to $C_8$ alkylene, $S(O)_n$, O, $CR_3R_4$ or CQ;
n is 0, 1 and 2;
$R_3$ and $R_4$ are individually hydrogen, $C_1$ to $C_6$ alkyl, $C_1$ to $C_6$ alkoxy or together form a divalent ring of 3 to 7 carbon or carbon and oxygen atoms wherein any two adjacent carbon atoms can also be part of a fused aromatic ring system;
Q is O, $NOR_5$ or $CY_2$;
$R_5$ is $C_1$ to $C_6$ alkyl, arylalkyl or substituted arylalkyl;
Y is hydrogen, halogen or $C_1$ to $C_6$ alkyl;
Z is oxygen or sulfur; and
n is 1 or 2.

7. A compound in accordance with claim 6 wherein:
$R_1$ and $R_2$ are individually $C_2$ to $C_4$ alkyl;
X is $S(O)_n$, O, $CR_3R_4$ or CQ;
$R_3$ and $R_4$ are individually hydrogen, $C_1$ to $C_6$ alkyl, $C_1$ to $C_6$ alkoxy, or together form a divalent ring of 5 to 7 carbon atoms; and
$R_5$ is $C_1$ to $C_6$ alkyl.

8. A compound in accordance with claim 6 wherein:
$R_3$ and $R_4$ are individually hydrogen or $C_1$ to $C_6$ alkyl;
Q is O, $NOR_5$ or $CCl_2$; and
Z is oxygen.

9. 2,2-bis[4-[(ethoxy)(propylthio)phosphoryloxy]phenyl]propane.

10. bis[4-[(ethoxy)(propylthio)phosphoryloxy]phenyl]sulfide.

11. An insecticidal and miticidal composition comprising an acceptable carrier and as the active toxicant, a pesticidally effective amount of a compound of the formula:

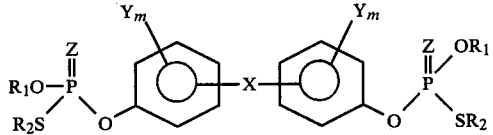

wherein:
$R_1$ and $R_2$ are individually $C_1$ to $C_6$ alkyl;

X is $C_2$ to $C_8$ alkylene, $S(O)_m$, O, $CR_3R_4$ or CQ;

n is 0, 1 or 2;

$R_3$ and $R_4$ are individually hydrogen, $C_1$ to $C_6$ alkyl, $C_1$ to $C_6$ alkoxy or together form a divalent ring of 3 to 7 carbon or carbon and oxygen atoms wherein any two adjacent carbon atoms can also be part of a fused aromatic ring system;

Q is O, $NOR_5$ or $CY_2$;

$R_5$ is $C_1$ to $C_6$ alkyl, arylalkyl or substituted arylalkyl;

Y is hydrogen, halogen or $C_1$ to $C_6$ alkyl;

Z is oxygen or sulfur; and m is 1 or 2.

12. A composition in accordance with claim 11 wherein:

$R_1$ and $R_2$ are individually $C_2$ to $C_4$ alkyl;

X is $S(O)_n$, O, $CR_3R_4$ or CQ;

$R_3$ and $R_4$ are individually hydrogen, $C_1$ to $C_6$ alkyl, $C_1$ to $C_6$ alkoxy, or together form a divalent ring of 4 to 6 carbon atoms; and $R_5$ is $C_1$ to $C_6$ alkyl.

13. A composition in accordance with claim 12 wherein:

$R_3$ and $R_4$ are individually hydrogen or $C_1$ to $C_6$ alkyl;

Q is O, $NOR_5$ or $CCl_2$; and

Z is oxygen.

14. A composition in accordance with claim 11 wherein the active toxicant is 2,2-bis[4-[(ethoxy)(propylthio)phosphoryloxy]phenyl]propane.

15. A composition in accordance with claim 11 wherein the active toxicant is bis[4-[(ethoxy)(propylthio)phosphoryloxy]phenyl]sulfide.

* * * * *